(12) United States Patent
Parker et al.

(10) Patent No.: US 11,857,215 B2
(45) Date of Patent: Jan. 2, 2024

(54) CIRCUMCISION DEVICE

(71) Applicant: Innovative Medical Technology (Pty) Ltd, Cape Town (ZA)

(72) Inventors: Cyril Norman Parker, Cape Town (ZA); Elisabeth Regina Parker, Cape Town (ZA); Jared Mark Vorster, Cape Town (ZA); David Christopher Wiseman, Cape Town (ZA)

(73) Assignee: INNOVATIVE MEDICAL TECHNOLOGY (PTY) LTD., Cape Town (ZA)

( * ) Notice: Subject to any disclaimer, the term of this patent is extended or adjusted under 35 U.S.C. 154(b) by 0 days.

(21) Appl. No.: 17/746,595

(22) Filed: May 17, 2022

(65) Prior Publication Data

US 2022/0273328 A1 Sep. 1, 2022

Related U.S. Application Data

(63) Continuation of application No. 16/492,496, filed as application No. PCT/IB2018/051397 on Mar. 5, 2018, now Pat. No. 11,357,538.

(30) Foreign Application Priority Data

Mar. 10, 2017 (ZA) .................................. 2017/01743

(51) Int. Cl.
*A61B 17/326* (2006.01)
*A61B 17/28* (2006.01)

(52) U.S. Cl.
CPC .......... *A61B 17/326* (2013.01); *A61B 17/282* (2013.01)

(58) Field of Classification Search
CPC ....... A61B 17/326; A61B 17/32; A61B 17/00; A61B 17/282

(Continued)

(56) References Cited

U.S. PATENT DOCUMENTS 3,669,115 A 6/1972 Melges
3,706,312 A 12/1972 Melges
(Continued)

FOREIGN PATENT DOCUMENTS

CN 1083695 A 3/1994
CN 203873839 U 10/2014
(Continued)

OTHER PUBLICATIONS

Austrian Patent Office, International Search Report and the Written Opinion in International Application No. PCT/IB2018/051397 (dated Jun. 13, 2018).

(Continued)

*Primary Examiner* — Wade Miles
*Assistant Examiner* — Bridget E. Rabaglia
(74) *Attorney, Agent, or Firm* — Leydig, Voit & Mayer, Ltd.

(57) ABSTRACT

A circumcision device is provided by the present invention. The device comprises two jaws configured to crush a foreskin between them along a crush region transverse to a foreskin and transverse to a general direction in which a penis being circumcised extends. The jaws are movable between an open inoperative position and a closed operative position in which a clamping and crushing force may be exerted to promote hemostasis within the crush region. The device includes a cutting assembly capable of traversing and severing a crushed foreskin within or adjacent the crush region. The invention extends to a glans penis protector comprising a handle separable from a transverse glans penis engaging cover so that the handle can be separated from the glans penis engaging cover during a circumcision procedure.

8 Claims, 5 Drawing Sheets

(58) Field of Classification Search
USPC .......................................................... 606/118
See application file for complete search history.

(56) References Cited

U.S. PATENT DOCUMENTS

| | | | |
|---|---|---|---|
| 7,303,567 B1 | 12/2007 | Smith | |
| 2007/0060928 A1* | 3/2007 | Dave | A61B 17/326 |
| | | | 606/118 |
| 2013/0310844 A1 | 11/2013 | Marotte | |
| 2018/0206876 A1* | 7/2018 | Souaida | A61B 17/326 |

FOREIGN PATENT DOCUMENTS

| | | |
|---|---|---|
| CN | 104207826 A | 12/2014 |
| CN | 204683718 U | 10/2015 |
| GB | 837252 | 6/1960 |
| WO | WO 2014/094005 A1 | 6/2014 |
| WO | WO 2015/155724 A1 | 10/2015 |

OTHER PUBLICATIONS

China National Intellectual Property Administration, Office Action for Chinese Patent Application No. 2018800301594 (dated Mar. 16, 2022).
Saudi Arbia Patent Office, Substantive Examination Report Notification for co-pending SA Appication No. 522441625, dated 16/11/1444 (dated Jun. 5, 2023)

* cited by examiner

CIRCUMCISION DEVICE

CROSS-REFERENCE TO RELATED APPLICATIONS

This patent application is a continuation of U.S. application Ser. No. 16/492,496, filed on Sep. 9, 2019, which claims the priority of International Application No. PCT/IB2018/051397, filed on Mar. 5, 2018. This application claims foreign priority to South African Application No. 2017/01743, filed on Mar. 10, 2017, which is incorporated by reference herein.

TECHNICAL FIELD

This invention relates to a circumcision device for conducting circumcision of a male person, ranging from infants to adult males. More particularly, the invention relates to a circumcision device that is preferably made as a single use device to avoid the transfer of infection from one person to another.

BACKGROUND

Circumcision of male persons is carried out for any one of a number of different reasons including religious and health reasons.

Human immunodeficiency virus (HIV) is a blood-borne virus that affects millions of people each year. The majority of worldwide infections have occurred in sub-Saharan Africa, where 19.2 million individuals were reported HIV-positive in 2014.

Male circumcision has been shown to decrease a man's chances of contracting HIV from an HIV positive female partner by of the order of 60%. Based on this, circumcision as a method of combating the contracting of HIV has the potential to prevent many new infections each year. This drastic reduction has prompted a push to circumcise approximately 30 million adult males by 2021 in an environment in which less than 30% of males in Africa are circumcised.

One of the 2020 strategic targets of UNAIDS is that 27 million men in high prevalence settings are voluntarily medically circumcised, as part of an integrated service for men.

The circumcision process has remained largely unaltered for the past few decades. A Gomco clamp has been in use since 1935 as a surgical assist instrument. The Gomco clamp has a protective bell and an axially movable clamping plate co-operating with it. Since about 1954 a Mogen clamp has also been used with the clamp having two flat blades that open approximately 3 mm and between which the foreskin is to be clamped transversely. The name Mogen clamp is a general term for a style of clamp and there are several different manufacturers of specific models. Both of these clamps operate to crush the foreskin along a line adjacent to which the cut is to be made and they each promote hemostasis after a clamping time period of the order of 5 minutes. Both of these are surgical assist instruments require the use of a hand held scalpel to complete the circumcision.

As an alternative to the clamping and crushing procedure to promote hemostasis, a freehand incision (classical) may be used, usually by a surgeon, to perform a circumcision using a hand held scalpel with the cutting being followed by the introduction of sutures.

Despite success of the Gomco and Mogen clamps within the United States, they are not suitable devices for mass circumcision programs such as in Sub-Saharan Africa. Using these two devices is also not without risks. The glans is not visible in either instance, or in the case of the Gomco clamp palpable, and the glans can be severed, as has happened with the use of both the Gomco and the Mogen clamps.

Other surgical assist instruments include those sold under the trade names Unicirc, Simple Circ, and CircumQ.

The Gomco and Mogen clamps have the disadvantage that they are re-usable devices whereas the WHO (World Health Organization) requires that a device should be single use only, and it must actively resist attempts to reuse it.

Furthermore, the Gomco and the Mogen Clamps as well as all other surgical assist devices and instruments rely upon the utilization of a hand held scalpel during the surgery. Due to the massive number of circumcisions that clinicians will be required to perform, many of which could be on HIV positive patients, there is a serious concern about exposing doctors, other clinical personnel and patients to any sharp devices. There is a statistically significant concern that a scalpel used in performing a surgical circumcision, could pose a threat to the health of the clinicians and patients, if they accidentally cut themselves with a blade that previously contacted HIV positive blood.

It should be noted that non-surgical assist circumcision devices including rings and clamps known as the Prepex, Shangring, Taraclamp, Ismailclamp, Plastibell, and Alisclamp would also be required to be single use devices. Plastic devices generally need to be left on the body for 5 to 7 days after which time they have to be removed. A device that needs to be left in place for an extended period of time is preferably not used due to excessive complications with scheduling follow up visits for the removal of the device. Additionally, there is a concern that the popularity of the entire circumcision program could be adversely affected by a foul smell that may accompany wearing the device under conditions in the skin begins to die and decompose which also increases the risk of infection with bacteria such as tetanus.

As regards published material describing attempts to fulfill the requirements of a single use circumcision device, international publication number WO2014094005 describes a circumcision device having a central glans penis locating member having a divergent outer crushing surface cooperating with the periphery of a crush aperture in a crush plate. The locating member and crush plate are axially movable relative to each other so that a gap between the crushing surface and crush aperture can be varied to effect crushing of foreskin that is positioned between them in a well-known manner. The means for effecting axial movement in this case is a pair of diametrically opposite screw threaded members located on opposite sides of the central glans penis locating member. In this instance single use is achieved by making the diametrically opposite screw threaded members that control the gap in the crush zone between the crushing surface and crush aperture such that they cannot be released sufficiently to introduce a subsequent foreskin after a first foreskin has been removed from the crush area.

A similar arrangement is described in international publication number WO2015155724 in which relative axial movement is achieved using a single screw threaded wing nut cooperating with a central tubular body having a glans penis locating end and an opposite operating end at which the wing nut is located. In this instance single use is achieved by making the central tubular body such that it cannot be released sufficiently to introduce a subsequent foreskin after a first one has been removed from the crush area.

However, in each of the latter two cases it is possible to dislocate or release the glans penis locating member. This may be considered to be a disadvantage in resulting in too many loose or separate components for disposal after completion of a procedure which is open to manipulation and possible attempts at re-use of components. Also multiple components require disposal as compared to disposal of one assembled instrument.

Also, neither of the latter two cases addresses the possible dangers of using separate scalpels or the like and their construction actually necessitates that a separate scalpel or the like be used to sever the foreskin adjacent the crush line. Still further, both of them are relatively complex and accordingly costly.

In order to provide for the number of circumcisions that will be necessary to impede the spread of HIV, a safe, reliable, cost effective and quick circumcision device and method are required that do not require the use of a separate scalpel or the like.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY

In accordance with a first aspect of this invention there is provided a circumcision device comprising two jaws configured to crush a foreskin between them along an elongated crush region that is transverse to a foreskin and transverse to a general direction in which a penis being circumcised extends, the jaws being movable between a first open inoperative position and a closed operative position in which a clamping and crushing force may be exerted on a foreskin positioned between the jaws to promote hemostasis within the elongated crush region; a mechanism interconnecting the jaws such that they are movable between the first open inoperative position in which one end of a gap between the jaws is open to allow for introduction of a transverse foreskin to move along the jaws to a central region thereof and the closed operative position in which the mechanism interconnects the jaws at both ends thereof and the jaws exert, in use, a crushing force on foreskin within the elongated crush region, the circumcision device being characterized in that it includes a cutting assembly movable from one end region of the jaws towards an opposite end region thereof relative to the elongated crush region so as to be capable of traversing and severing a crushed foreskin within or adjacent the elongated crush region and wherein the cutting assembly includes a carrier movable along a length of one of the jaws from a first end region thereof to a second end region thereof.

Further features of the first aspect of the invention provide for the carrier to have a releasable stop maintaining it in a position corresponding to the first open inoperative position of the jaws; for the jaw with which the cutting assembly is associated to be in the form of a jaw assembly composed of an arm supporting the carrier and a flat surgical blade attached to the carrier with the blade being guided for movement between a guide surface of the arm and a guide surface of an insert received within the arm with a cutting edge of the blade co-operating in the closed operative position with a face of the other jaw within the elongated crush region so that the face serves as a cutting block for the blade; and for the carrier to have a catch component in co-operating relationship with a complimentary co-operating catch formation on an associated jaw assembly so that the carrier becomes irreversibly locked in its terminal position at the second end region of the jaws following a cutting action to thereby effectively prevent attempts at using the device for a subsequent circumcision.

Still further features of the invention provide for the mechanism to include formations providing a hinged interconnection at a first end of the jaws wherein the hinged connection cannot be disengaged when the jaws are in their first or second inoperative positions or their closed operative positions; for second ends of the jaws to be interconnected by a lever assembly including an operating lever and a pivotally attached connecting lever connected at an opposite end to the second end of one jaw with the operating lever having pivot lugs that are receivable in co-operating receiving formations associated with the other jaw so that the operating lever and connecting lever can be used by engaging the pivot lugs in the co-operating receiving formations associated with the other jaw to close an opening between the ends of the two jaws after introduction of a foreskin transversely between the jaws and to move the jaws together into the closed operative position; for the levers to be configured to lock the jaws in their closed operative positions in releasable manner by means of an over-centre locking mechanism; and for the pivot lugs to be receivable in the co-operating receiving formations associated with the other jaw in a non-releasable manner in order to obscure and deter or render substantially impractical a second or subsequent use of the device by providing a second open inoperative position in which the connecting lever and the operating lever substantially inhibit the introduction of a foreskin to a position between the jaws.

In accordance with a second aspect of this invention there is provided a glans penis protector for assisting in the avoidance of damage to a glans penis during a surgical circumcision procedure that involves the crushing of a foreskin adjacent the glans penis to promote hemostasis in the crushed region of the foreskin followed by severing of the foreskin at or immediately adjacent the crushed region on a distal side thereof to remove the distal portion of the foreskin, the glans penis protector comprising a handle having a distal operating end region and a transverse glans penis engaging cover at its proximal end wherein an attachment of the handle to the glans penis engaging cover is capable of being parted so that the handle can be separated from the glans penis engaging cover during a circumcision procedure.

Further features of this aspect of the invention provide for the attachment of the handle to the glans penis engaging cover to be formed integral with the glans penis protector in which event the attachment of the handle to the glans penis engaging cover is preferably frangible; for the glans penis protector to be made of an injection moulded plastic material; for the attachment of the handle to a distal surface of the glans penis engaging cover to be by way of a pair of spaced necks immediately adjacent the distal surface and preferably located in recesses in the distal surface; for the glans penis engaging cover to be contoured in a direction transverse to the handle so as to co-operate with a distal end region of a glans penis in use, for the handle to be generally flat optionally with one or more apertures through it and with a width of the handle being orientated such that a proximal end region thereof can be temporarily accommodated in an narrow gap between two crushing jaws of a circumcision device having a pair of jaws between which a foreskin may be crushed adjacent a glans penis preparatory to circumcision; and for an axially extending probe to be provided at the proximal end of the handle with the probe preferably having a rounded end for use in releasing adhesions to the glans penis safely.

A method of carrying out a circumcision of a foreskin of a patient using the circumcision device and a glans penis protector according to the first and second aspects of the invention therefore comprises releasing adhesions to a glans penis of a patient as may be required; covering the glans penis with a glans penis engaging cover of a glans penis protector as defined above; locating a portion of the foreskin of the patient to be severed over the handle of the glans penis protector; moving the foreskin and glans penis protector transversely through an opening between corresponding ends of the jaws of a circumcision device as defined above with the glans penis engaging cover immediately adjacent to the jaws on a proximal side thereof and the handle passing between the jaws, parting the handle from the glans penis engaging cover to leave it on the proximal side of the jaws opposite said required portion of the foreskin to be severed, engaging the pivot lugs on the operating lever with the co-operating receiving formations in the associated jaw, operating the mechanism to move the jaws from their first open inoperative position to their closed operative position in order to crush the foreskin in an elongated crush region between the jaws; allowing the crushed foreskin to remain in that condition for a time period selected to promote hemostasis; moving the cutting assembly from its initial position in one end region of the jaws to an opposite end region of the jaws to effect severing of the foreskin crushed between the jaws or immediately adjacent a distal side thereof; releasing the mechanism sufficiently to permit withdrawal of the attached foreskin from the circumcision device; and removing the glans penis engaging cover.

Other preferred steps in the method of carrying out a circumcision will be quite apparent to those of ordinary skill in the art and will, in any event, be more apparent from what follows.

In order that the above and other features of the invention may be more fully understood, one embodiment of the invention will now be described, by way of example only, with reference to the accompanying drawings.

DETAILED DESCRIPTION OF EMBODIMENTS

It should be mentioned at the outset that all the components of the device and the glans penis protector of this invention other than the blade which will generally be made of surgical steel and the connecting lever which will generally be made from sheet metal can, although not necessarily, be made as injection moulded plastic parts designed and made according to requirements.

Figure 1:
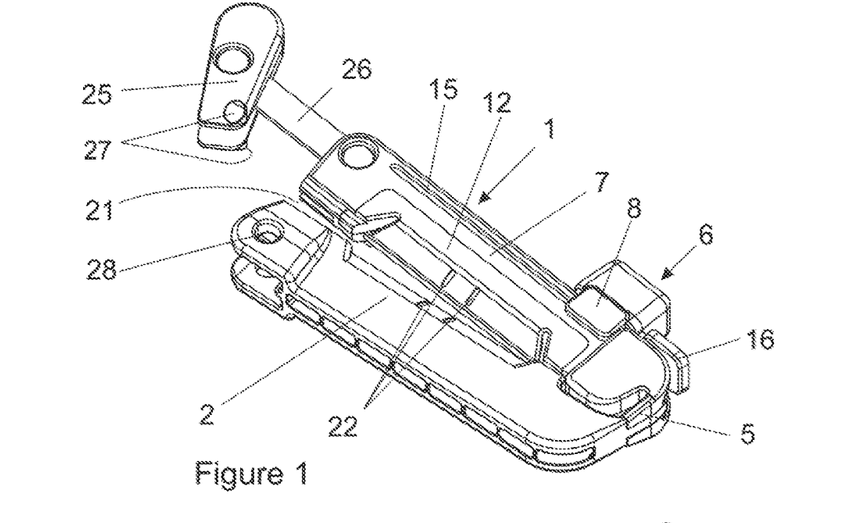
FIG. 1 is a three-dimensional view of one embodiment of circumcision device according to the first aspect of the invention with the lever assembly in its initial disengaged condition preparatory to use of the device and the jaws in their first open inoperative positions.
Figure 2:
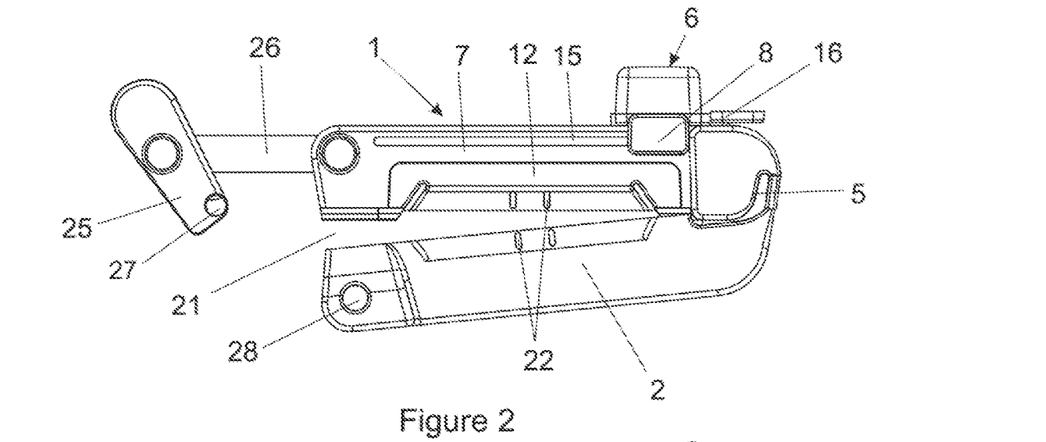
FIG. 2 is an elevation thereof from one side.
Figure 5:
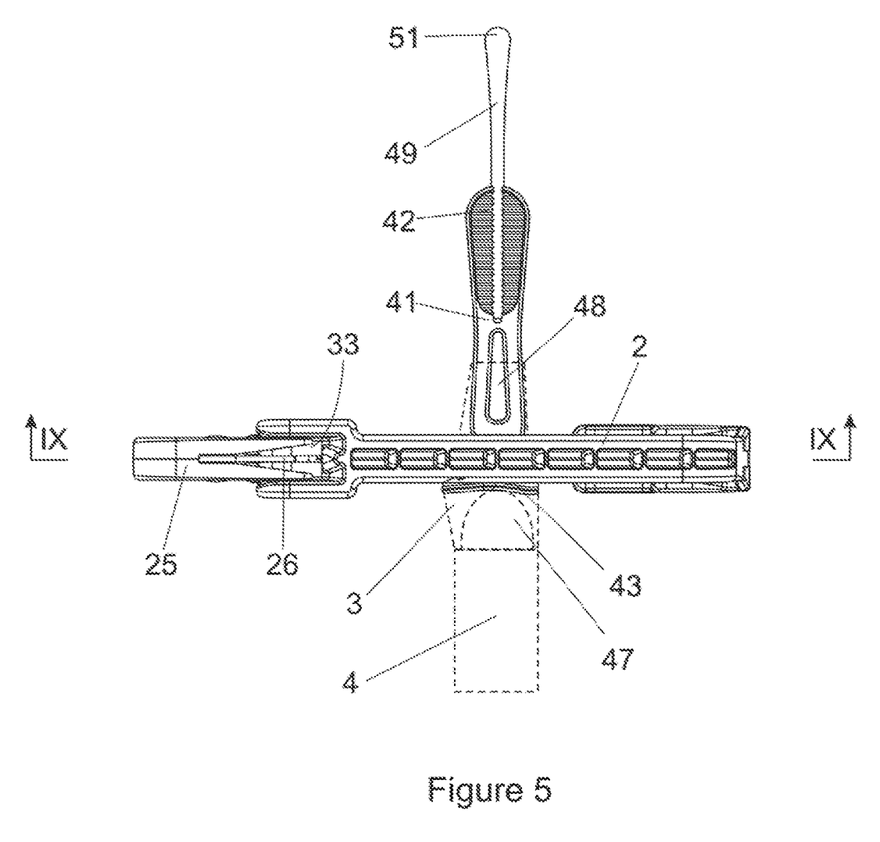
FIG. 5 is an underneath view of the circumcision device illustrated in FIG. 4.
Figure 6:
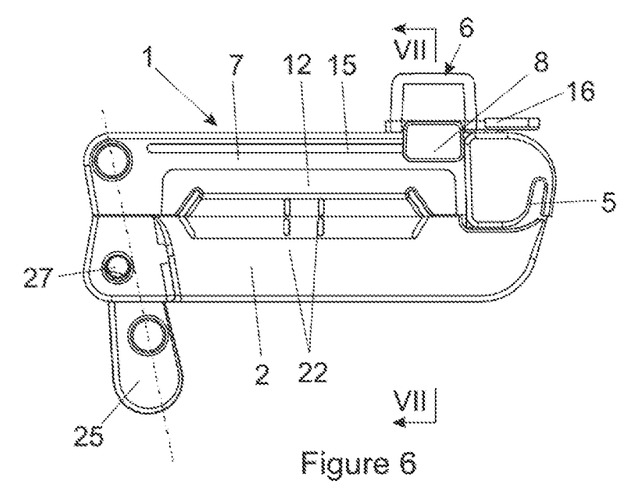
FIG. 6 is a similar elevation of the circumcision device with the jaws in their closed operative position being a clamped crushing position.

In the embodiment of the invention illustrated in the drawings, a circumcision device comprises two jaws (1, 2) configured to crush a foreskin between them along an elongated crush region that is transverse to a foreskin (3) and transverse to a general direction in which a penis (4) (see FIG. 5) being circumcised extends. The jaws (1, 2) are movable about a hinged connection at one end region (5) thereof between a first open inoperative position illustrated in FIGS. 1 to 3 and a closed operative position in which a clamping and crushing force is exerted on a foreskin positioned between the jaws (1, 2) to promote hemostasis within the elongated crush region as illustrated in FIG. 6.

Figure 3:
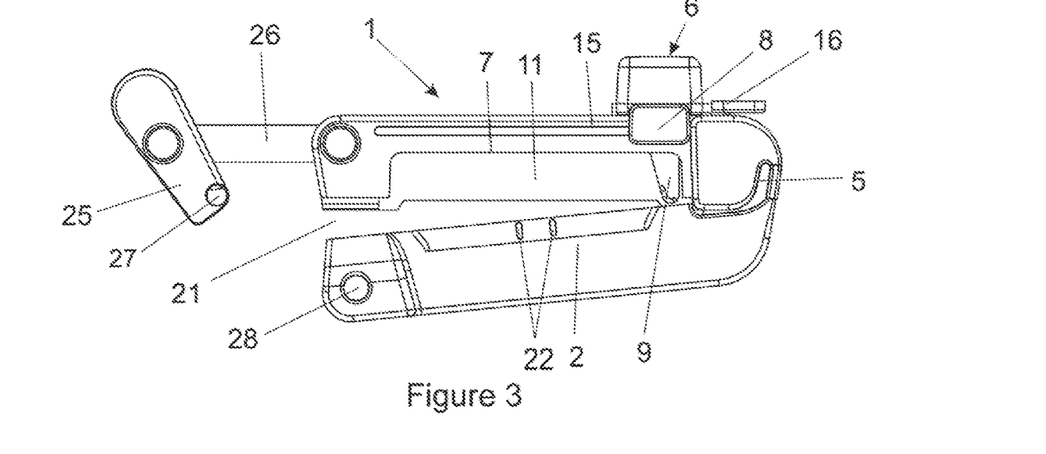
FIG. 3 is a similar elevation thereof with an insert removed from its supporting arm to expose the surgical blade.
Figure 4:
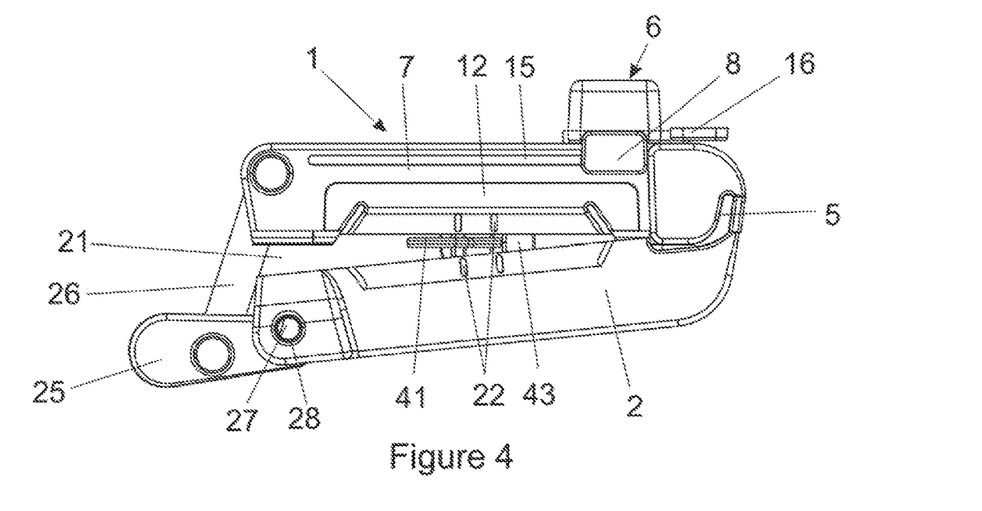
FIG. 4 is a similar elevation but illustrating the lever assembly in a closed first open inoperative position and showing the glans penis protector in position.
Figure 7:
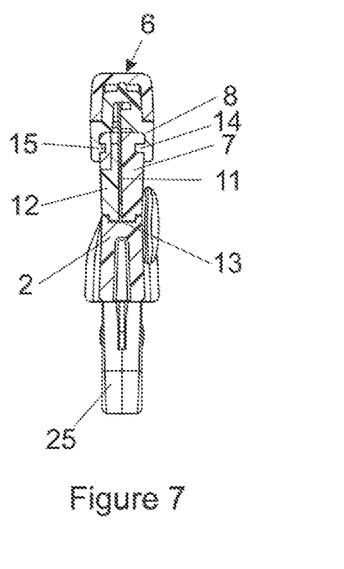
FIG. 7 is a cross-section taken along line VII to VII in FIG. 6.

The first jaw (1) with which a cutting assembly (6) is associated is in the form of a jaw assembly composed of an arm (7) supporting a carrier (8) that has attached to it a flat surgical blade (9) (see FIG. 3). The blade (9) is guided for movement in its own plane between a guide surface (11) of the arm (7) and a parallel guide surface of an insert (12) received within the arm. A cutting edge of the blade (9), as shown in FIG. 7, co-operates in the closed operative position with a crushing face (13) of the second jaw (2) within the elongated crush region such that the crushing face (13) serves as a cutting block for the blade (9).

The carrier (8) has, in this embodiment of the invention, a recess accommodating an outer edge of the arm (7) with two inwardly directed lips (14) located in grooves (15) extending along the length of the arm (7) to confine movement of the carrier (8) from a first end region of the arm to a second end region of the arm. A releasable hinged stop (16) maintains the carrier in a position corresponding to the first open inoperative position of the jaws (1, 2). The carrier (8) also has a catch component (17) in co-operating relationship with a complimentary co-operating catch formation (18) on the insert so that the carrier (8) becomes irreversibly locked in its terminal position at the second end region of the jaw assembly following a cutting action. This effectively prevents attempts at using the device for a subsequent circumcision, resulting in "use-once" functionality.

A mechanism interconnects the jaws (1, 2) such that they are movable between their first open inoperative position in which one end of a gap (21) between the jaws is open to allow for the lateral introduction of a transverse foreskin to move along the jaws to a central region thereof that is clearly indicated by suitable markers (22) and the closed operative position. The mechanism includes the hinged interconnection that is provided at a first end region (5) of the jaws (1, 2) wherein the hinged connection is configured so that it cannot be disengaged when the jaws (1, 2) are in their closed operative positions or second inoperative positions as described below.

As regards the second ends of the jaws, they are interconnected by a lever assembly that includes an operating lever (25) pivotally attached to a connecting lever (26) at one end and pivotally connected at an opposite end to the second end of one jaw, the first jaw (1) in this instance, with the operating lever having co-axial pivot lugs (27) that are receivable in co-operating receiving formations in the form of apertures (28) associated with spaced flanges of the second jaw (2). The arrangement is such that the operating lever (25) and connecting lever (26) can be used, when the pivot lugs (27) are engaged in their co-operating apertures (28), to obstruct a lateral opening to the gap between the second ends of the two jaws (1, 2) to prevent the subsequent introduction of a foreskin transversely between the jaws. The lever assembly is configured to lock the jaws (1, 2) in the closed operative position in releasable manner by means of an over-centre locking mechanism as will be apparent from FIG. 6.

The pivot lugs (27) are receivable in the co-operating receiving formations in the form of apertures (28) associated with the second jaw in a substantially non-releasable manner in order to obscure and deter, or render substantially impossible, a second or subsequent use of the device. By so doing, a second open inoperative position is provided in which the connecting lever and the operating lever together obscure the entrance to the gap between the jaws (1, 2) in their released positions following a circumcision in a first use and substantially prevent the transverse introduction of a foreskin to a position between the jaws (1, 2).

Figures 8, 9, 10:
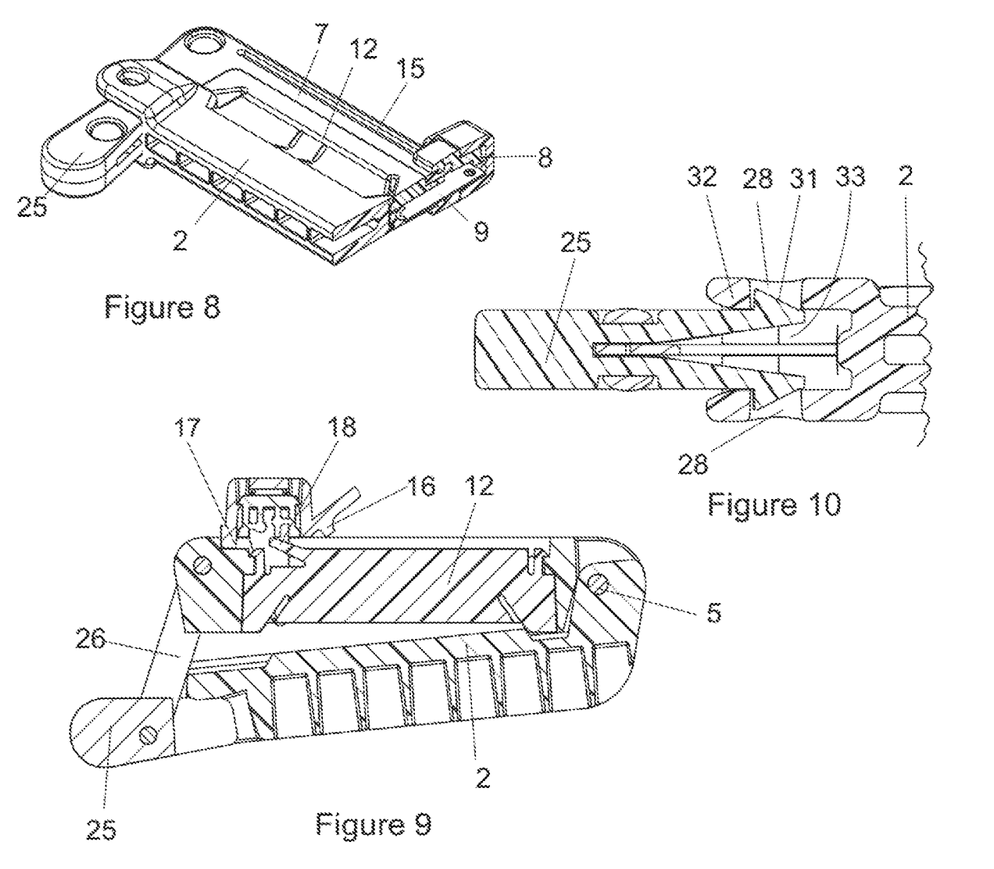
FIG. 8 is a three-dimensional sectioned view of the circumcision device illustrated in FIG. 6 showing the section along line VII to VII.
FIG. 9 is a sectional elevation taken along line IX to IX in FIG. 5.
FIG. 10 is a sectional detail showing the pivot lugs on the operating lever received in co-operating receiving formations in the associated jaw in a non-releasable manner.
Figure 11:
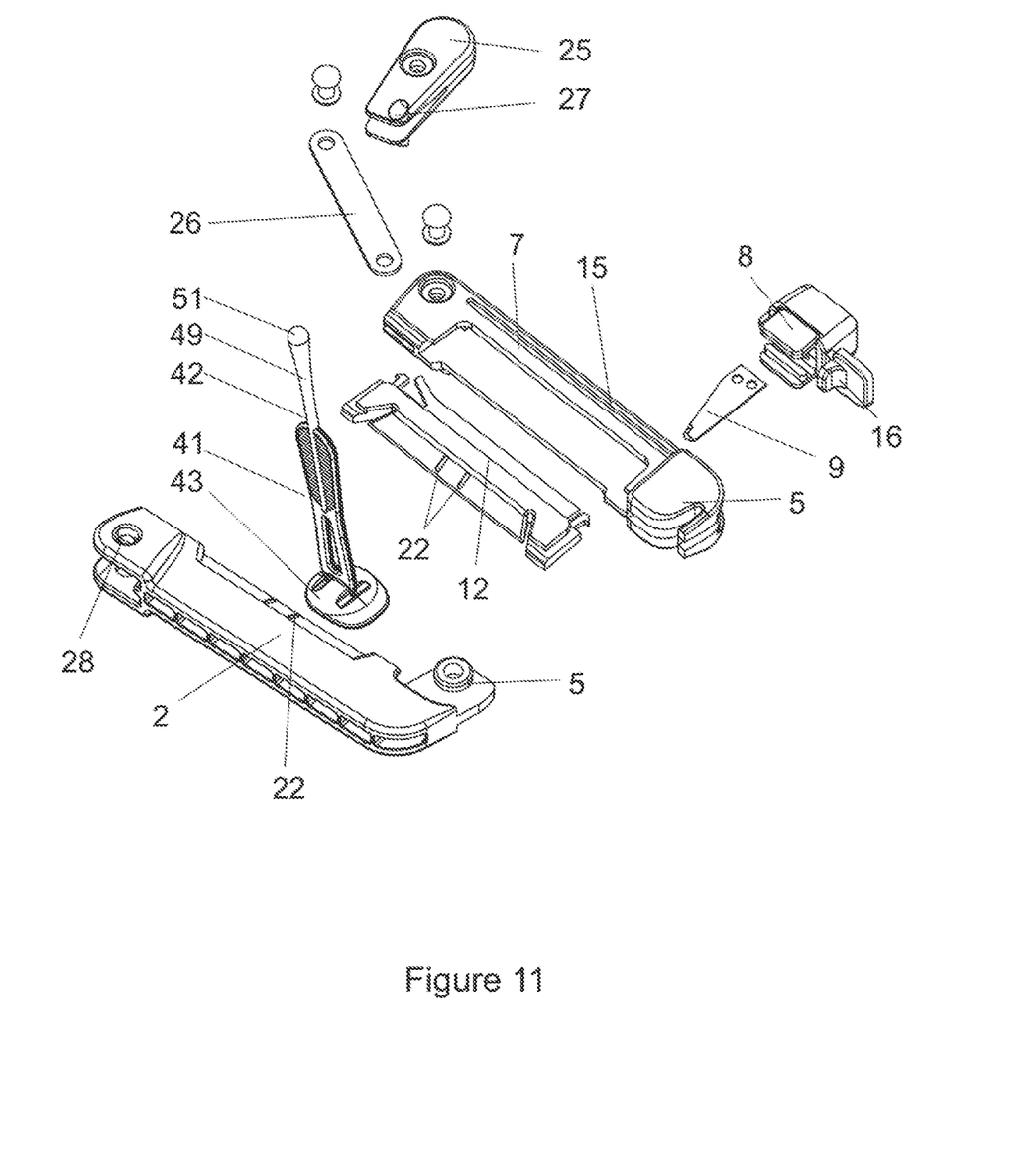
FIG. 11 is a three dimensional exploded view of this embodiment of the first aspect of the invention and of one embodiment of a glans penis protector according to the second aspect of the invention.
Figures 12, 13, 14, 15:
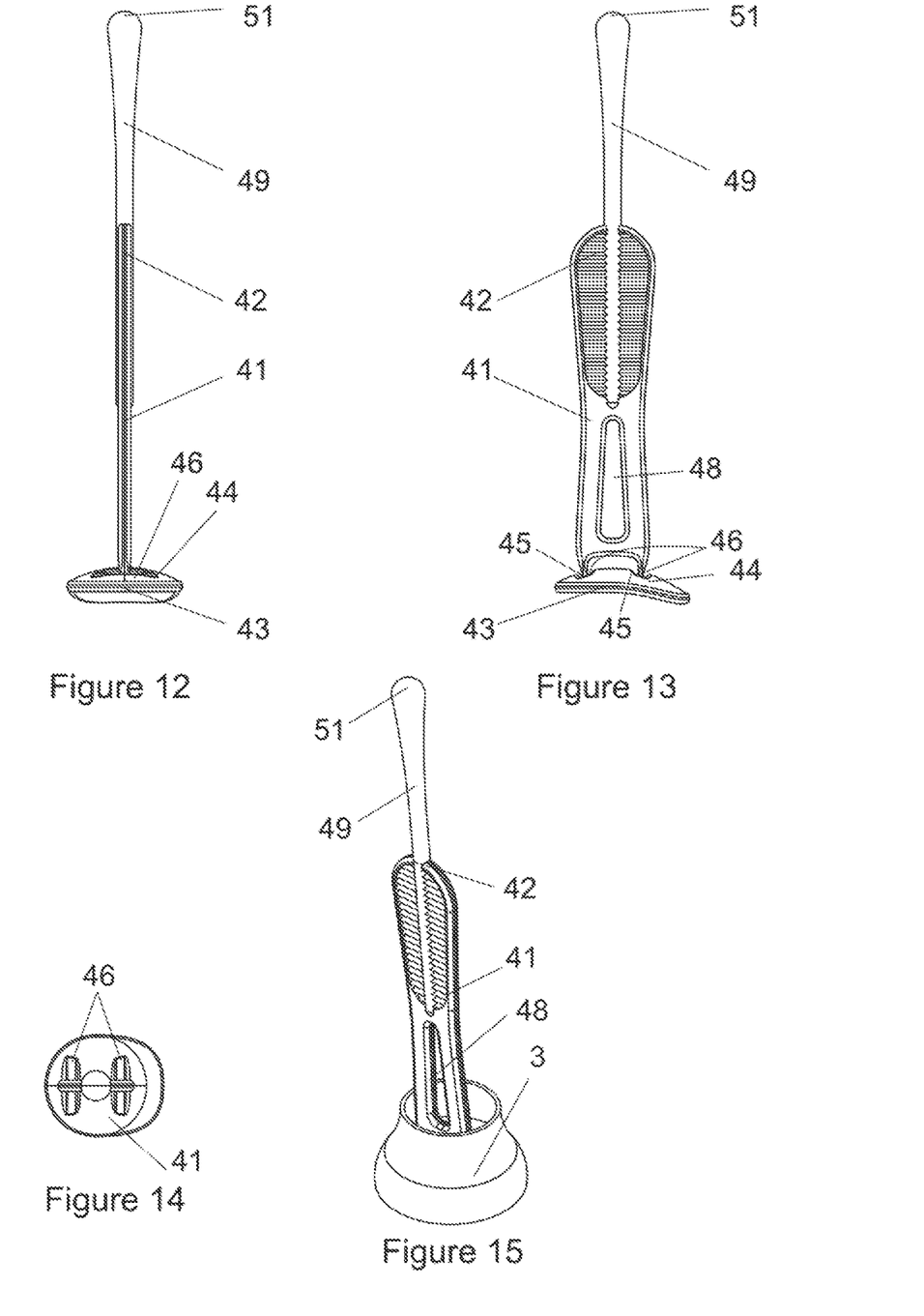
FIG. 12 is a side view of this embodiment of the glans penis protector.
FIG. 13 is a front elevation thereof.
FIG. 14 is an end view thereof from the handle end of the protector.
FIG. 15 is a three-dimensional illustration illustrating a simulated foreskin in position on the glans penis protector.

Introduction of the pivot lugs is achieved in this instance by providing bevelled ends (31) (see FIG. 10) to the pivot lugs that may be forced into a space between two spaced flanges (32) of the second jaw (2). The relevant region of the operating lever (25) may be bifurcated, as indicated by numeral (33), so that the natural "give" in the plastics materials allows the pivot lugs to be urged into position between the two spaced flanges and to snap into their final positions as illustrated in FIG. 10. The arrangement is such that withdrawal of the lugs is resisted so as to prevent separation of the operating lever from the second jaw.

The jaws (1, 2) are thus interconnected at both ends to exert a crushing force on a foreskin within the elongated crush region when the jaws are in their closed operative positions.

The cutting assembly is of course movable from one end region (the first end region) of the jaws towards an opposite end region (the second end region) thereof relative to the elongated crush region so as to be capable of traversing and severing a crushed foreskin within the elongated crush region.

Turning now to the second aspect of the invention, a glans penis protector for assisting in the avoidance of damage to a glans penis during a surgical circumcision procedure is particularly illustrated in FIGS. 4, 5 and 11 to 15 and comprises a handle (41) having a proximal operating end region (42) and a transverse generally disc shaped glans penis engaging cover (43) at its distal end. The attachment of the handle (41) to the glans penis engaging cover (43) is capable of being parted so that the handle can be separated from the glans penis engaging cover during a circumcision procedure.

In this embodiment of the second aspect of the invention the glans penis protector is made of injection moulded plastics material and is formed integral with the glans penis engaging cover integral with the handle. The attachment of the handle to a proximal surface (44) of the glans penis engaging cover (43) is by way of a pair of laterally spaced necks (45) located immediately adjacent the bottom of spaced in recesses (46) the proximal surface so that the necks can break off below the proximal surface (44). The glans penis engaging cover (43) is contoured in a direction transverse to the handle so as to co-operate with a distal end region of a glans penis (47) in use (see FIG. 5). The handle is generally flat with one or more apertures (48) through it and with a width of the handle being orientated such that a distal end region thereof can be accommodated in a narrow gap between two crushing jaws of a circumcision device in the first open inoperative position described above.

The functionality of the protector may be enhanced by providing an axially extending probe (49) at the proximal end of the handle with the probe having a rounded end (51) for use in ensuring that the main function of the probe of the glans protector is to release adhesions safely. Normally a straight forceps that would typically be reusable is used to do this. This has the danger that it may be placed accidentally in the urethra. Adhesions are normal in infants and young children, where the foreskin has not yet been retracted. The release needs to happen before the circumcision.

Steel forceps can cause penetrating injury to the glans, the mucosa, and can accidentally be inserted into the urethra which can tear. The probe has sufficient length to reach the corona at the end of the glans. The design of the glans protector and probe as a single unit, has the benefit of safely releasing the adhesions, protecting the glans and reducing the chance of accidental insertion into the urethra and still further complying with the single use requirement.

A method of carrying out a circumcision of a foreskin of a patient using the circumcision device and a glans penis protector as described above thus comprises removal of any adhesions between the glans and the foreskin using the probe (49) on the back of the glans protector, and covering a glans penis of a patient with a glans penis engaging cover of a glans penis protector as described above with the handle extending generally away from the penis. The required portion of the foreskin (3) of the patient is located over the handle (41) and the foreskin (3) and handle (41) are moved transversely through an opening between corresponding ends of the jaws (1, 2) of a circumcision device as described above with the glans penis engaging cover (43) immediately adjacent to the jaws (1, 2) and the handle (41) passing between the jaws (1, 2). The handle (41) can then be aligned with the markers (22). At that stage the handle (41) is broken away from the glans penis engaging cover (43) to leave it on the side of the jaws opposite that on which the required portion of the foreskin to be removed is located.

The connecting lever (26) and operating lever (25) are moved into position to engage the pivot lugs (27) on the operating lever (25) with the co-operating receiving formations in the associated jaw. The mechanism is then operated to move the jaws (1, 2) from their first open inoperative position to their closed operative position in order to crush the foreskin in an elongated crush region between the jaws (1, 2) and that the crushed condition is allowed to persist for a period of time that is typically of the order of 5 minutes to promote hemostasis and a condition favourable to the severing of the foreskin by means of the cutting assembly.

The releasable hinged stop (16) is then disengaged and the carrier (8) moved along the arm (7) to cause the blade (9) to sever the foreskin by co-operation with the crushing face of the other jaw. The face of the other jaw thereby acts as a cutting block for the blade. The cutting assembly is thus moved from its initial position in one end region of the arm (7) and jaws (1, 2) to an opposite end region to effect severing of the foreskin crushed between the jaws (1, 2). At the end of its travel along the arm (7) the carrier (8) becomes locked in its terminal position by virtue of the catch component (17) moving into co-operating relationship with the complimentary co-operating catch formation (18) on the arm so that the carrier (8) becomes irreversibly locked in its terminal position as described above.

Release of the mechanism to the second open inoperative position is then carried out so that the jaws (1, 2) move apart sufficiently to permit withdrawal of the attached foreskin from the circumcision device. The glans penis engaging cover can then be removed from the penis.

Numerous variations to the embodiments of the two aspects of the invention described above are possible within the scope in the invention. Indeed the glans penis protector need not be used at all as the circumcision device may be used on its own. The glans penis protector may also be used on its own, and in particular in combination with existing circumcision devices where its functionality in protecting the glans penis during a cut of foreskin performed by a blade may be particularly valuable. Devices such as, for example, a Mogen clamp or Mogen clamp-type devices which include a pair of opposing jaws usable to clamp a foreskin to be severed therebetween so as to promote hemostasis as is known in the art. However, it will be appreciated that it may be used with any device or instrument that crushes a patient's foreskin, including a classical forceps guided circumcision. During use of any such device, the glans penis protector may reduce the risk of the head of the glans being crushed or cut by protecting the head and urethral opening of the penis. The gland penis protector may also be used with the Gomco clamp, Accucirc, any tissue forceps (whether serrated, toothed, flat or smooth) or the like which in use crushes the foreskin and/or mucosa of a patient and/or release adhesions prior to performing the required surgical procedure.

Devices such as a Gomco clamp, Accucirc, tissue forceps or any similar or related device may also be used with the glans penis protector, where it may shield the glans penis from accidental interaction with a blade performing a cut of the foreskin. While use of the glans penis protector separately will not provide a single use circumcision device, it will provide a single-use glans penis protecting device if the handle is severed from the engaging cover as described above during use.

Use of the glans penis protector together with other a known Morgen clamp-type circumcision device may therefore involve the release of adhesions to a glans penis of a patient as may be required, covering the glans penis with the glans penis engaging cover of the glans penis protector, locating a portion of the foreskin of the patient to be severed over the handle of the glans penis protector, moving the foreskin and glans penis protector transversely through an opening between corresponding ends of jaws of the Morgen clamp-type circumcision device, with the glans penis engaging cover immediately adjacent to the jaws on a proximal side thereof and the handle passing between the jaws, and parting the handle from the glans penis engaging cover to leave it on the proximal side of the jaws opposite said required portion of the foreskin to be severed. The jaws of the Morgen clamp-type circumcision device may then be closed as normal so that the foreskin of the patient is crushed therebetween. The device may further be used as normal, by for example allowing the crushed foreskin to remain in that condition for a time period selected to promote hemostasis. The foreskin may then be cut using the known method for that device, for example by a normal scalpel in a transverse direction across the foreskin. The jaws may then be opened as known to permit withdrawal of the attached foreskin from the circumcision device. The glans penis engaging cover may then be removed and discarded.

It will be appreciated that the glans penis protector may be produced in a number of different sizes to accommodate a variety of glans penis sizes. This may at least partially allow for the device to be used for different age groups.

In use with other circumcision devices that are not Morgen clamp-type devices, it will be apparent that the procedure will be different, as required for the specific type of device.

The circumcision device provided by this invention has many features that are considered to be advantageous in that it may be configured as a single use device and does not require a long-duration on the body The device may be used to eliminate the use of separate sharp objects such as a scalpel and thereby protect patients and medical staff from risks of accidental wounds with the possibility of exposure to blood and infection.

The device may be designed to be inexpensive to manufacture.

Throughout the specification and claims unless the contents requires otherwise the word 'comprise' or variations such as 'comprises' or 'comprising' will be understood to imply the inclusion of a stated integer or group of integers.

What is claimed is:

1. A glans penis protector comprising a handle having a proximal operating end region and a transverse glans penis engaging cover at its distal end, wherein an attachment of the handle to the glans penis engaging cover is capable of being parted so that the handle can be separated from the glans penis engaging cover during a circumcision procedure, wherein the attachment of the handle to a proximal surface of the glans penis engaging cover is located in a recess in the proximal surface of the glans penis engaging cover, and
   wherein the attachment of the handle to the proximal surface of the glans penis engaging cover is located in spaced recesses in the proximal surface of the glans penis engaging cover by way of a pair of spaced necks immediately adjacent the proximal surface of the glans penis engaging cover.

2. The glans penis protector as claimed in claim 1, wherein the attachment of the handle to the glans penis engaging cover is formed integral with the glans penis protector.

3. The glans penis protector as claimed in claim 1, wherein the attachment of the handle to the glans penis engaging cover is frangible.

4. The glans penis protector as claimed in claim 1, wherein the glans penis engaging cover is contoured in a direction transverse to the handle so as to co-operate with a distal end region of a glans penis in use.

5. The glans penis protector as claimed in claim 1, wherein the handle is generally flat and a width of the handle is capable of being orientated such that the proximal operating end region thereof can be temporarily accommodated in a narrow gap between two jaws of a circumcision device preparatory to circumcision.

6. The glans penis protector as claimed in claim 1, wherein an axially extending probe is provided at a proximal end of the handle with the axially extending probe having a rounded end for use in releasing adhesions to the glans penis.

7. A method of carrying out a circumcision of a foreskin of a patient using a glans penis protector as claimed in claim 1 together with a circumcision device having jaws, the method comprising:
- releasing adhesions to a glans penis of a patient;
- covering the glans penis with the glans penis engaging cover of the glans penis protector;
- locating a portion of the foreskin of the patient to be severed over the handle of the glans penis protector;
- moving the foreskin and glans penis protector transversely through an opening between the jaws of the circumcision device until the glans penis engaging cover is immediately adjacent to the jaws with the handle passing between the jaws;
- parting the handle from the glans penis engaging cover so as to leave the cover on a side of the jaws opposite from said portion of the foreskin to be severed;
- crushing the foreskin in an elongated crush region between the jaws;
- allowing the crushed foreskin to remain in that condition for a time period selected to promote hemostasis;
- severing the foreskin crushed between the jaws;
- releasing the jaws; and
- removing the glans penis engaging cover.

8. The method as claimed in claim 7, wherein the method includes releasing adhesions to the glans penis of the patient by way of a rounded end of a probe provided at a proximal end of the handle of the glans penis protector.

* * * * *